(12) United States Patent
Su et al.

(10) Patent No.: US 7,998,496 B2
(45) Date of Patent: Aug. 16, 2011

(54) USE OF MOLT-ACCELERATING COMPOUNDS, ECDYSTEROIDS, ANALOGS THEREOF, AND CHITIN SYNTHESIS INHIBITORS FOR CONTROLLING TERMITES

(75) Inventors: Nan-Yao Su, Davie, FL (US); James Edward King, Carmel, IN (US); Paul Allen Neese, Westfield, IN (US)

(73) Assignee: University of Florida Research Foundations, Inc., Gainesville, FL (US)

( * ) Notice: Subject to any disclaimer, the term of this patent is extended or adjusted under 35 U.S.C. 154(b) by 1075 days.

(21) Appl. No.: 10/589,770

(22) PCT Filed: Feb. 17, 2005

(86) PCT No.: PCT/US2005/005014
§ 371 (c)(1),
(2), (4) Date: Apr. 30, 2007

(87) PCT Pub. No.: WO2005/079572
PCT Pub. Date: Sep. 1, 2005

(65) Prior Publication Data
US 2008/0242647 A1      Oct. 2, 2008

Related U.S. Application Data

(60) Provisional application No. 60/546,356, filed on Feb. 19, 2004.

(51) Int. Cl.
*A01N 25/32* (2006.01)
(52) U.S. Cl. ......... 424/406; 43/132.1; 424/84; 424/405; 424/409; 424/410; 424/DIG. 11; 514/597; 514/615
(58) Field of Classification Search .................. None
See application file for complete search history.

(56) References Cited

U.S. PATENT DOCUMENTS

| 5,427,786 A | 6/1995 | Payne et al. |
| 5,558,862 A | 9/1996 | Corbin et al. |

(Continued)

FOREIGN PATENT DOCUMENTS

CN        1399876        *  3/2003
(Continued)

OTHER PUBLICATIONS

Su et al-Monitoring /Baitging Station—Journal of Economic Entomology, Aug. 1995, vol. 88 # 4, pp. 932-936.*

(Continued)

*Primary Examiner* — Neil Levy
(74) *Attorney, Agent, or Firm* — Saliwanchik, Lloyd & Eisenschenk

(57) ABSTRACT

The subject invention relates in part to the oral administration of ecdysteroids for controlling subterranean termites. Preferred ecdysteroids for use according to the subject invention are ecdysone, certain ecdysone analogs, and 20-hydroxyecdysone, for example. In some preferred embodiments, one or more of these compounds is used in a termite bait in combination with one or more chitin synthesis inhibitors (CSI), such as hexaflumuron and/or noviflumuron. The subject invention also relates to mixtures comprising these two active ingredients. The ecdysteroid analog or molt-accelerating compound (MAC) typically induces a preliminary molting event in termite workers, which then allows the CSI to further disrupt the molt and cause mortality. The combination of these active ingredients, causing accelerated molting together with inhibition of chitin synthesis, is surprisingly shown herein to enhance activity against termites, as compared to either group of compounds alone.

4 Claims, 4 Drawing Sheets

U.S. PATENT DOCUMENTS

| | | | |
|---|---|---|---|
| 5,573,760 | A | 11/1996 | Thorne et al. |
| 5,753,249 | A | 5/1998 | Schwab |
| 5,815,090 | A | 9/1998 | Su |
| 6,052,066 | A | 4/2000 | Su |
| 6,093,415 | A | 7/2000 | Karr et al. |
| 6,123,756 | A | 9/2000 | Poppen et al. |
| 6,214,364 | B1 | 4/2001 | Schwab |
| 6,248,159 | B1 | 6/2001 | Poppen et al. |
| 6,370,812 | B1 | 4/2002 | Burns et al. |
| 6,397,516 | B1 | 6/2002 | Su |
| 6,404,210 | B1 | 6/2002 | Su |
| 6,857,223 | B2 | 2/2005 | Su |
| 2003/0108585 | A1 | 6/2003 | Roe et al. |
| 2003/0177689 | A1 | 9/2003 | Su |
| 2003/0180343 | A1 | 9/2003 | Su |

FOREIGN PATENT DOCUMENTS

| | | |
|---|---|---|
| CN | 1402994 | 3/2003 |
| FR | 2716625 | 9/1995 |
| JP | 05-112405 | 5/1993 |
| JP | 06-256111 | 9/1994 |
| JP | 2000-159620 | 6/2000 |
| JP | 2003-246705 | 9/2003 |
| WO | WO 85/02340 | 6/1985 |
| WO | WO 93/23998 | 12/1993 |
| WO | WO 98/34481 | 8/1998 |
| WO | WO 03/082000 | 10/2003 |
| WO | WO 03/092376 | 11/2003 |
| WO | WO 2004/0041257 | 5/2004 |

OTHER PUBLICATIONS

Carlson, G., et al., "Synergistic Insecticides Containing N'-tert-butyl-N-(4-ethylbenzoyl)-N'-(3,5-dimethylbenzoyl) Hydrazine," *Chemical Abstract Service*, 1993, Columbus, Ohio. Abstract Only.

Darvas, B., et al., "Developmental Disturbances in Different Insect Orders Caused by an Ecdysteroid Agonist, RH 5849," *Journal of Economic Entomology*, 1992, pp. 2107-2112, vol. 85, No. 6. Abstract Only.

Dhadialla, T. S, et al., "New Insecticides with Ecdysteroidal and Juvenile Hormone Activity," *Annual Review of Entomology*, 1998, pp. 545-569, vol. 43.

Donati, C., et al. "Pantetina, diabete e aterosclerosi. Indagine clinica su 1045 pazienti," *La Clinica Terapeutica*, Mar. 31, 1989, pp. 411-422, vol. 128, No. 6.

Haverty, M. I., "The Proportion of Soldiers in Termite Colonies: A List and a Bibliography (Isoptera)," *Sociobiology*, 1977, pp. 199-216, vol. 2, No. 3.

Hrdý, I., et al., "Development of Superfluous Soldiers Induced by Juvenile Hormone Analogues in the Termite, *Reticulitermes Lucifugus Santonensis*," *Insectes Sociaux*, 1972, pp. 105-109, vol. 19, No. 2.

Kozlova, T., et al., "Spatial Patterns of Ecdysteroid Receptor Activation During the Onset of *Drosophila* Metamorphosis," *Development*, 2002, pp. 1739-1759, vol. 129, No. 7.

Lüscher, M., et al., "Experimentelle Auslösung Von Häutungen Bei Der Termite *Kalotermes flavicollis* (Fabr.)," *Journal of Insect Physiology*, 1958, pp. 341-345, vol. 1, No. 4.

Lüscher, M., "Hormonal Control of Caste Differentiation in Termites," *Annals of the New York Academy of Sciences*, 1960, pp. 549-563, vol. 89.

Ma, Y., et al., "Tebufenozide-Containing Compound Insecticide," *Chemical Abstract Service*, 2004, pp. 6143-6150, Columbus, Ohio. Abstract Only.

Monteagudo, E. J., "Evaluation of Halofenozide as an Effective Bait Against the Eastern Subterranean Termite (Isoptera: Rhinotermitidae)," #59 *Florida Entomological Society 2002 Annual Meeting Abstracts*, 2002, Ft. Lauderdale, FL.

Obrosova, I. G., et al. "Biochemical Mechanisms of the Hypolipidemic Effect of Pantethine in Insulin-Independent Diabetes," *Khimiko-Farmatsevticheskii Zhurnal*, Jan. 1, 1988, pp. 1302-1309, vol. 22, No. 11.

Raina, A.K., et al., "Ecdysone Agonist Halofenozide Affects Corpora Allata and Reproductive Physiology of the Formosan Subterranean Termite, *Coptotermes Formosanus*," *Journal of Insect Physiology*, 2003, pp. 677-683, vol. 49.

Rojas, M., et al., "Bait Matrix for Delivery of Chitin Synthesis Inhibitors to the Formosan Subterranean Termite (Isoptera: Rhinotermitidae)," *Journal of Economic Entomology*, Apr. 2001, pp. 506-510, vol. 94, No. 2.

Sako, Y., et al. "Effect of glibenclamide on pancreatic hormone release from isolated perifused islets of normal and cysteamine-treated rats," *Metabolism, Clinical and Experimental*, Oct. 1, 1986, pp. 944-949, vol. 35, No. 10.

Su, N.-Y., et al., "Foraging Population and Territory of the Formosan Subterranean Termite (Isoptera:Rhinotermitidae) in an Urban Environment," *Sociobiology*, 1988, pp. 353-359, vol. 14, No. 2.

Su, N.-Y., et al., "Potential of Insect Growth Regulators as Termiticides: A Review," *Sociobiology*, 1990, pp. 313-328, vol. 17, No. 2. Abstract Only.

Su, N.-Y., et at., "Laboratory Evaluation of Two Chitin Synthesis Inhibitors, Hexaflumuron and Diflubenzuron, as Bait Toxicants Against Formosan and Eastern Subterranean Termites (Isoptera: Rhinotermitidae)," *Journal of Economic Entomology*, 1993, pp. 1453-1457, vol. 86, No. 5. Abstract Only.

Su, N.-Y., "Field Evaluation of a Hexaflumuron Bait for Population Suppression of Subterranean Termites (Isoptera: Rhinotermitidae)," *Journal of Economic Entomology*, 1994, pp. 389-397, vol. 87. Abstract Only.

Su, N.-Y., et al., "A Review of Subterranean Termite Control Practices and Prospects for Integrated Pest Management Programmes," *Integrated Pest Management Reviews*, 1998, pp. 1-13, vol. 3.

Su, N.-Y., "Baits as a Tool for Population Control of the Formosan Subterranean Termite," *Sociobiology*, 2003, pp. 177-192, vol. 41. Abstract Only.

Tunaz, H., et al., "Insect Growth Regulators for Insect Pest Control," *Turkish Journal of Agriculture and Forestry*, 2004, pp. 377-387, vol. 28, No. 6.

Uchida, M., et al., "Antagonistic Effect of 20-Hydroxy-ecdysone to an Insect Growth Regulator, Buprofezin, in *Nilaparvata Lugens Stål*," *Agriculture and Biological Chemistry*, 1986, pp. 1913-1916, vol. 50, No. 7.

Watabe, T., et al., "Synergistic Insecticides Containing Hydrazine and Benzoylphenylurea Derivatives," *Chemical Abstract Service*, 1995, Columbus, Ohio. Abstract Only.

Wing, K. D., et al., "RH 5849, a Nonsteroidal Ecdysone Agonist: Effects on Larval Lepidoptera," *Science*, 1988, pp. 470-472, vol. 241, No. 4864.

Xu, H., et al., "Mixed Synergistic Insecticide of Azadirachtin and RH-5849," *Chemical Abstract Service*, Columbus, Ohio. Abstract Only.

Hrdý, I., "Effect of Juvenoids on Termites and Honeybees," *Proceedings of the seventh International Congress of the IUSSI*, 1973, pp. 158-159, vol. 2, No. 3.

\* cited by examiner

USE OF MOLT-ACCELERATING COMPOUNDS, ECDYSTEROIDS, ANALOGS THEREOF, AND CHITIN SYNTHESIS INHIBITORS FOR CONTROLLING TERMITES

CROSS-REFERENCE TO RELATED APPLICATION

This application is the U.S. national stage application of International Patent Application No. PCT/US2005/005014, filed Feb. 17, 2005, which claims the benefit of U.S. Provisional Patent Application No. 60/546,356, filed Feb. 19, 2004, the disclosures of which are hereby incorporated by reference in their entireties, including all figures, tables and amino acid or nucleic acid sequences.

BACKGROUND OF THE INVENTION

Subterranean termites most often enter structures from the surrounding soil to feed on wood, or other cellulosic material, of the structure and its contents. If unchecked, termites can cause considerable damage. As a result, efforts to erect physical or chemical barriers to prevent the entrance of termites into a structure or to exterminate the termites after they have invaded a structure have proven a considerable expense to the public.

Subterranean termites construct an extensive foraging gallery beneath the soil surface. A single colony may contain several million termites with foraging territory extending hundreds of feet (Su, N.Y., R. H. Scheffrahn [1988] *Sociobiol.* 14(2):353-359). Because subterranean termites are cryptic creatures, their presence is not normally known until after some damage, foraging tubes, or live termites (such as swarmers) are found.

Currently, there are two basic approaches for the control of subterranean termites: preventive control and remedial control. In some of the United States, it is mandatory that the soil underlying the foundation of newly constructed buildings be pre-treated with a pesticide (also referred to herein as termiticide) to prevent termite infestation. However, the barrier often loses its continuity, and the currently available soil termiticides tend to lose their biological activity after a few years. Established termite colonies in the soil may then invade the structure if additional chemical is not applied beneath and around the structure.

When a house or other building is infested by subterranean termites, one option is to introduce termiticide around a building foundation by injection into soil underlying concrete foundations, drenching the soil surrounding the building perimeter, or a combination of both. This type of post-construction treatment is labor-intensive and may not adequately produce a continuous barrier. Other remedial treatments include spot treatments such as dusting or injecting termiticides (such s arsenic trioxide) within the walls of the building.

Some toxicants that have less environmental effect and that show activity against termites are known. However, prior to 1995, these toxicants were not used in conjunction with a method that efficiently and efficaciously delivered the toxicant to a target pest.

The introduction of the first commercial termite bait system, SENTRICON®, in 1995 drastically changed subterranean termite control practices. Unlike prior treatments, a monitoring-baiting program such as SENTRICON® is capable of eliminating the entire colony. See WO 93/23998, U.S. Pat. No. 6,370,812, and U.S. Pat. No. 6,397,516. Because of the target-specific approach, only a few grams of hexaflumuron are needed to eliminate a colony that may contain several hundred thousand termites (Su 1994, *J. Econ. Entomol.* 87:389-397). Due to its low environmental impact, hexaflumuron was the first compound to be registered under EPA's Reduced Risk Pesticide Initiative. The SENTRICON® system was the recipient of EPA's Presidential Green Chemistry Award in 2000.

There remains a need for additional termite toxicants that have little or no adverse environmental effects. For example, U.S. Pat. Nos. 5,753,249; 6,214,364; and 5,558,862 relate to methods of controlling insects by administering enzymes that disrupt ecdysteroid metabolic pathways.

Insects have an exoskeleton (made of mostly chitin and proteins) that protects them from external elements such as weather and natural enemies. The external cuticle, however, has to be shed periodically for continuous growth. Endocrine products, most notably brain hormone, juvenile hormone, and ecdysone (FIG. 1A), are known to regulate insect molting (Chapman 1976). Ecdysone is rapidly converted to 20-hydroxyecdysone (or "20E," FIG. 1B) following its release into the insect hemolymph (Nation 2002). The presence of juvenile hormone (JH), a sesquiterpenoid, ensures that insects retain the juvenile form (i.e. to molt from a younger larval stage to the next larval stage). As insects progressively molt, JH concentration decreases and may even be totally absent at the last larval instar. In the absence of JH, a larva then molts into pupa or adult stage.

The effects of JH, its analogs (JHAs), and mimicries (JHMs) on termites are well studied (Su and Scheffrahn 1990). JHAs and JHMs (referred to as juvenoids) are known to produce excessive soldier termites whose function is for colony defense. Because the soldier caste has to be fed by workers, termite colonies contain optimal proportions of the soldier caste (Wilson 1971, Haverty 1977). It has been proposed that juvenoids, which induce excessive soldier formation, may be used to disrupt the integrity of a termite society, leading to the destruction of the entire colony (Haverty 1977, Hrdy and Krecek 1972, Hrdy 1973). However, further studies revealed that juvenoids are effective only against termite species with a lower natural soldier proportion, such as *Reticulitermes* species) (Su and Scheffrahn 1990). *Coptotermes* species, which have a relatively high proportion of soldiers, include an unusually large proportion of economically important termites in the world (Su 2003).

One relatively recent development in subterranean termite control is the use of termite baits containing chitin synthesis inhibitors (CSIs) such as hexaflumuron or noviflumuron to eliminate the vast colony of subterranean termites (Su 1994, Su 2003). In order to eliminate an entire colony of termites, the active ingredient (AI) for a bait has to be non-repellent, slow-acting, and its lethal time has to be dose-independent so that the AI is distributed throughout the colony by termites before the onset of death (Su and Scheffrahn 1998). Insect growth regulators (IGRs) such as juvenoids and CSIs satisfy all these three requirements. However, many IGRs are species-specific (Su 2003). CSIs generally inhibit the biosynthesis of chitin, but its complete process remains poorly understood (Nation 2002).

U.S. Pat. No. 6,093,415 relates to synergistic effects between juvenoid insecticides and CSIs in termite baits. Ecdysone and analogs thereof are not mentioned.

While juvenoids and CSIs are well investigated for their potentials for termite control, limited information is available for even the normal function of ecdysone in termites. Lüscher and Karson (1958) and Lüscher (1960), while trying to determine the role, if any, that ecdysone plays in the normal biology of termites (and not in attempts to control termites), reported that injection of ecdysone alone or in combination with JH induced a normal pseudogate molting of the lower termites, *Kalotermes flavicollis*. Since their studies, there has been no known investigation of the effects of ecdysone in or on termites.

Synthetic versions of ecdysteroids have been used to control some insect pests of agricultural importance, but not termites. These analogs typically mimic the activity of 20E to cause premature molting (Wing et al. 1988). Toward the end of the molting under normal condition, 20E is degraded and excreted, thus allowing the eclosion hormone to complete the process (Nation 2002). The analogs, however, are more stable than 20E and are not easily degraded or excreted (Wing et al. 1998). Consequently, their continuing presence in insect hemolymph interferes with complete molting and causes hyperecdysonism (premature molting without a successful termination). Hence, these analogs can be referred to as ecdysteroid agonists (Dhadialla et al. 1998).

U.S. Pat. Nos. 6,123,756 and 6,248,159 relate to wood preservative for protecting wood against dry-wood-destroying insects, such as the house longhorn (*Hylotrupes bajulus*), woodworm (*Anobium punctatum*), and bark beetle (*Lyctus brunneus*). Those patents relate to lumber (not insect bait) treated with a combination of a juvenile hormone and an ecdysone agonist. Subterranean termites are different from drywood termites, are not dry-wood-destroying insects, and are not mentioned or suggested in those patents. See, e.g., U.S. Pat. No. 5,027,546, which describes a system intended for use on above ground termites, i.e. drywood termites, by freezing them with liquid nitrogen.

Positive results were obtained when the ecdysteroid agonist RH-5849 was tested against some insect species (Darvas et al. 1992), but limited information is available regarding potential effects of ecdysteroid agonists against termites. Raina et al. (2003) reported that one such agonist, halofenozide, may impact the reproductive physiology of alate nymphs of *C. formosanus*. However, for use in baits to eliminate a subterranean termite colony, the active ingredient in the bait has to be lethal to the worker caste, which makes up the majority of the colony population. Alate nymphs, which make up only a small portion of a colony, eventually leave the nest to start a new colony somewhere else. However, they do not forage like workers. Thus, eliminating the young, alate nymphs would not impact the overall colony population and its damaging potential.

Halofenozide is one of several molt-accelerating compounds (MACs) owned by Dow AgroSciences. Halofenozide has activity on *Lepidoptera* and some *Coleoptera* species. In the urban pest management business, halofenozide is currently registered under the trade name MACH 2™ in the United States for control of white grub and surface feeding *Lepidoptera* in residential and commercial lawns and golf courses.

There have been some limited reports of testing of halofenozide against termites. For example, an abstract from the Florida Entomological Society 2002 Annual Meeting (Monteagudo & Su [2002]), related to preliminary results of a choice test conducted to examine preference, deterrence, and lethality of the insect growth regulator bait halofenozide on workers of the eastern subterranean termites (*Reticulitermes flavipes*). The corresponding "ten-minute paper" stated that halofenozide was evaluated in a choice test for its potential as a bait toxicant against the eastern subterranean termite. Feeding blocks composed of wood slices were vacuum-impregnated with halofenozide at various concentrations, with feeding deterrence occurring at concentrations greater than 4,000 ppm. There was also a USDA inhouse memo that mentioned RH-0345 (a.k.a. halofenozide) as having a significant effect on ovarian development in alates and nymphs of *C. formosanus*. However, the effect, at low doses used in the test, was temporary. That memo also discussed the use of a juvenile hormone analog to induce the formation of mutant soldiers. The USDA termite program in New Orleans has also examined halofenozide for potential ovicidal effects in *C. formosanus* and presented results in 10-minute oral presentation at the 2001 meeting of the Entomological Society of America (paper 0269).

There have been no known reports regarding testing ecdysteroids or analogs thereof, other than halofenozide, for termite control. Furthermore, there are no known tests regarding the combination of the CSI+MAC (or ecdysteroids) classes of chemistry against insects, including termites.

BRIEF SUMMARY OF THE INVENTION

The subject invention relates in part to controlling termites by the use of a chitin synthesis inhibitor (CSI), such as hexaflumuron and/or noviflumuron, and an ecdysteroid (and analogs thereof) or a molt-accelerating compound (MAC), such as halofenozide. The subject invention also relates to mixtures comprising these two active ingredients. The MAC/ecdysteroid analog induces a preliminary molting event in a termite worker, which then allows the CSI to disrupt the molt and cause mortality. The combination of these active ingredients, causing accelerated molting together with inhibition of chitin synthesis, is surprisingly shown herein to enhance activity against termites, as compared to either group of compounds alone.

The subject invention relates in part to the oral administration of ecdysteroids and analogs thereof to foraging subterranean worker termites. After eating ecdysteroids of the subject invention, termites were induced to molting. However, they could not complete the molting and eventually died. This is the first time that fatal effects of ecdysone against termites were demonstrated. Preferred ecdysteroids for use according to the subject invention are ecdysone, analogs thereof, and 20-hydroxyecdysone, for example. When used with a CSI according to the subject invention, the combination surprisingly provides faster (and more complete) efficacy against termites than either insecticide group alone.

The subject invention includes all combinations of any given MAC insecticide (such as halofenozide and/or tebufenozide) together with any given CSI for control of all termite species. The subject invention also includes any of various types of formulations and delivery systems (e.g., baits, dusts, and liquid formulations).

DETAILED DESCRIPTION OF THE INVENTION

Figure 1A:
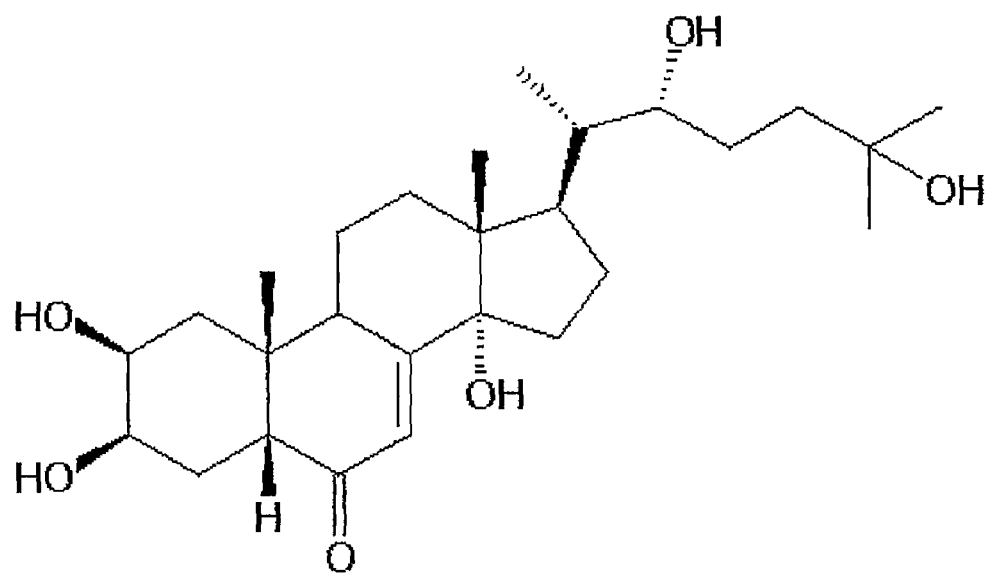
FIG. 1A shows the chemical structure of ecdysone.
Figure 1B:
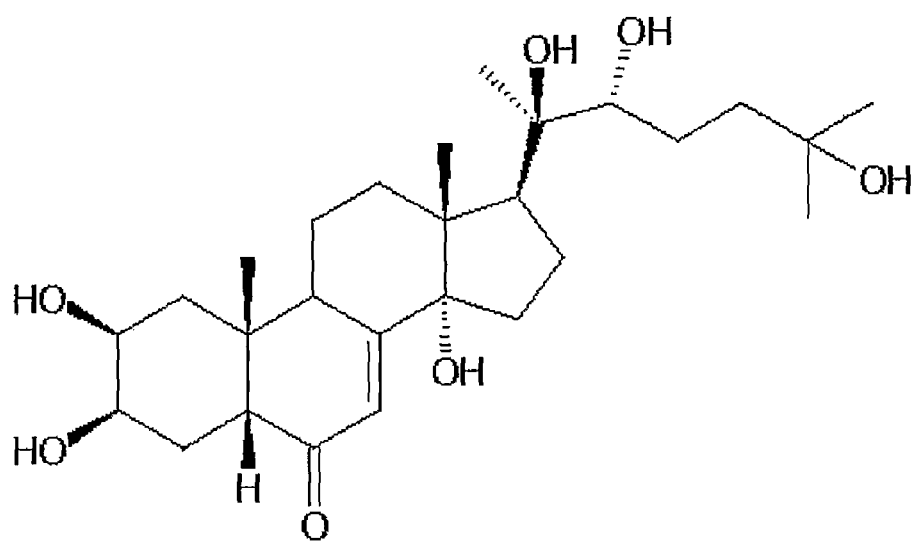
FIG. 1B shows its active hormone 20-hydroxyecdysone.

The subject invention relates in part to controlling termites by the use of a chitin synthesis inhibitor (CSI), such as hexaflumuron and/or noviflumuron, and an ecdysteroid (and analogs thereof) or a molt-accelerating compound (MAC), such as halofenozide. The subject invention also relates to mixtures comprising these two active ingredients. The MAC/ecdysteroid analog induces a preliminary molting event in a termite worker, which then allows the CSI to disrupt the molt and cause mortality. The combination of these active ingredients, causing accelerated molting together with inhibition of chitin synthesis, is surprisingly shown herein to enhance activity against termites, as compared to either group of compounds alone.

The subject invention includes all combinations of any given MAC insecticide (such as halofenozide and/or tebufenozide) together with any given CSI for control of all termite species. The subject invention also includes any of various types of formulations and delivery systems (e.g., baits, dusts, and liquid formulations).

The subject invention also relates in part to the oral administration of ecdysteroids and analogs thereof for controlling subterranean termites. When exposed to (after eating or otherwise ingesting) ecdysteroids of the subject invention, termites were induced to molting. However, they could not complete the molting and eventually died. This is the first known report of fatal effects of ecdysteroids against termites.

Compositions of the subject invention can also be used to cause other adverse (but desirable) effects on the target termites, such as cessation of feeding and overt toxicity in affected termites. In addition, an effective amount of the ecdysteroid can be used to induce molting; this is helpful when used to "synergize" or enhance the effects of a CSI, as discussed herein. The subject invention provides exciting new options for inhibiting termites (i.e., killing them and preferably the entire colony, making them sick, preventing them from feeding on wooden structures, and the like).

Preferred ecdysteroids for use according to the subject invention are ecdysone, analogs thereof, and 20-hydroxy-ecdysone ("20E" or "20E-ecdyson"; the by-product of ecdyson usually created inside insects), for example. However, other ecdysteroids, in addition to ecdysone and 20E, can be fed (and/or administered in food, provided in baits, and the like) to termites according to the subject invention, as explained in more detail below. When used with a CSI according to the subject invention, the combination surprisingly provides faster (and more complete) efficacy against termites than either insecticide group alone.

It was quite surprising to find that ecdysone and other analogs thereof provided excellent termite control. This discovery was completely unexpected and surprising, especially noting prior studies where injection of ecdysone into termites simply caused successful molting without any harmful effects. (Lüscher and Karson 1958; Lüscher 1960.) Thus, in some embodiments of the subject invention, the ecdysteroid component can be used without the CSI component. Halofenozide, also called RH-0345, is a coleopteran-specific variant of tebufenozide. In embodiments where the ecdysteroid (or analog) is used without a CSI, halofenozide is excluded from such embodiments. With that noted, "molt accelerating compounds" as used herein include natural and synthetic compounds, ecdysteroids, analogs thereof, halofenozide, and all related insecticides that are useful and functional for inducing accelerated and/or premature molting in termites.

Summarizing some of the other results reported herein, a series of laboratory trials were conducted to determine the survivorship and feeding response of eastern subterranean termites (EST), *Reticulitermes flavipes* (Kollar) in oral ingestion choice tests with halofenozide. Tests were also conducted to evaluate the potential additive/synergistic effects of halofenozide (at various concentrations) when combined with the chitin synthesis inhibitors hexaflumuron or noviflumuron. The combination of halofenozide plus a CSI insecticide caused enhanced efficacy when compared to either type of insecticide alone. The impact of halofenozide appeared greater when combined with hexaflumuron, although a boost in speed of activity was also seen in combination with noviflumuron. For 5000-ppm hexaflumuron, a concentration of 5000-ppm halofenozide was needed to cause significant additive effects within 26 days. Lower concentrations of halofenozide (2500-1250 ppm) enhanced 5000-ppm noviflumuron within 14 days. A smaller-scale study on the termite *Amitermes wheeleri* also showed that halofenozide can enhance efficacy when combined with CSI insecticide.

Figure 2A:
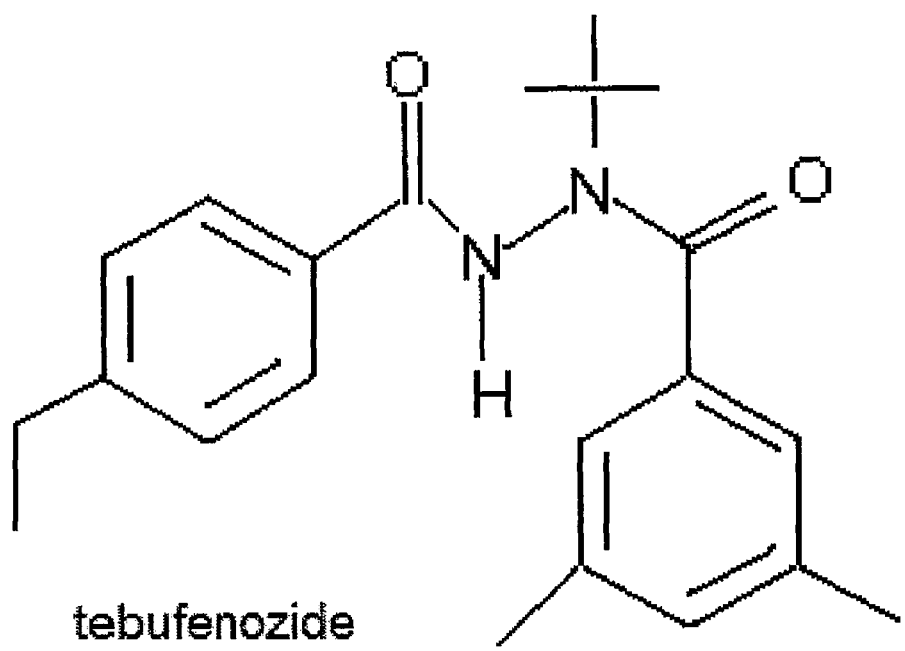
FIG. 2A shows the chemical structure of tebufenozide, an ecdysone analog.
Figure 2B:
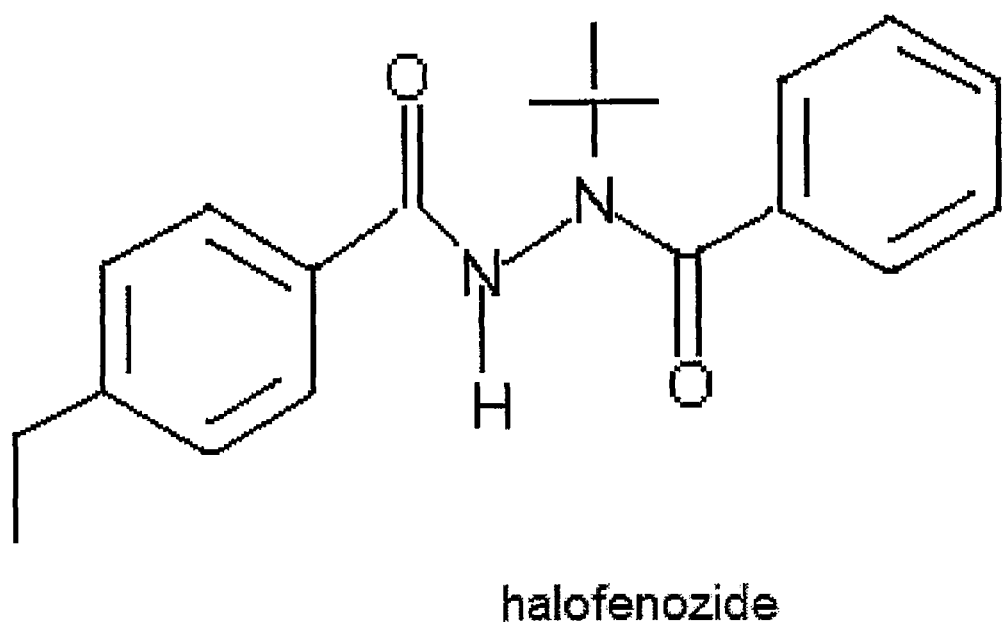
FIG. 2B shows the chemical structure of halofenozide.

Other examples of ecdysteroid analogs for use (or adaptable for use) according to the subject invention include tebufenozide, which is an insecticide originally designed for controlling lepidopteran pests. It does not affect natural populations of beneficial, predatory, and parasitic insects for the control of other insect pests. FIG. 2A shows the chemical structure of tebufenozide, from the 1996 *Farm Chemicals Handbook*. RH-5849 (1,2-dibenzoyl-1-tert-butylhydrazine) is a beetle-specific alternative to tebufenozide. Halofenozide, also called RH-0345, is a coleopteran-specific variant of tebufenozide. Halofenozide is also a preferred MAC for use with a CSI according to the subject invention. FIG. 2B shows the chemical structure of halofenozide. Some other ecdysteroid agonists include methoxyfenozide and chromafenozide. Thus, the subject invention can include the use of tebufenozide, tebufenozide analogues, RH-5849, and chromafenozide. Another possibility is methoxyfenozide or RH-2485.

It should be noted that while the term "MAC" is used throughout this specification, MACs can also be thought of as molt-inhibiting compounds. As described elsewhere herein, MACs can induce molting, but the molting is not completed. Thus, the term "molt-inhibiting" is also appropriate.

The "second" active ingredient (the "first" AI being a MAC, an ecdysteroid, or analog, of the subject invention) can preferably comprise chemicals that interfere with the formation of exo-cuticle such as the chitin synthesis inhibitors (CSIs). CSIs are known to interfere with the chitin synthesis procedure, but such procedure does not take place until insects produce ecdysone under a pre-determined, natural biological clock. Thus CSIs have to passively wait for the natural molting to take place. When synergistically used in combination with CSIs, ecdysteroids or ecdysteroid agonists can induce termites to molt (after oral ingestion) even where the termites ingest a sublethal dose (a dose that may not cause hyperecdysonism but will initiate molting), and then the molting process is inhibited by a CSI. Examples of preferred second AIs, as mentioned above, are hexaflumuron, noviflumuron, diflubenzuron, flufenoxuron, chlorfluazuron, bistrifluron, azadirachtin, lufenuron, and other acryl ureas, which can be impregnated or incorporated into cellulose material, for example, during the formulation of the toxicant-containing matrix.

The subject ecdysteroid or analog "AI" (active ingredient) can be used in conjunction with other toxicants or AIs (a "third" AI, for example). The subject ecdysone-type AIs and other preferred A's are slow-acting, lethal at concentrations which do not repel target insects, and capable of being combined with the matrix as described above.

It is intended that pests directly contacting or ingesting the subject toxicants will not be killed immediately but will travel to and/or through their colony to recruit other nestmates to the toxicant, thereby resulting in the control of large numbers of colony members. It is preferred that the pest die days, weeks, or even months after encountering the toxicant of the subject invention.

Compounds for use according to the subject invention can be used in the bait matrix of SENTRICON-like station housings, above-ground stations, and hermetically sealed baits. The subject compounds can be fed to foraging subterranean termite workers and delivered by them to nestmates of the same colony. (Unless specifically stated, when "termites" are referred to herein generically, such reference is to subterranean termites. Subterranean termites are different from drywood termites.)

Monitoring-baiting systems (like SENTRICON) and CSIs are relatively recent developments in subterranean termite control. Termite baits containing chitin synthesis inhibitors (CSIs), such as hexaflumuron or noviflumuron, can advantageously be used to eliminate the vast colony of subterranean termites (Su 1994, Su 2003), which is an accomplishment that could not be achieved by use of traditional liquid insecticides. The active ingredient (AI) for a bait has to be non-repellent, slow-acting, and its lethal time has to be dose-independent so that the AI is distributed throughout the colony by termites before the onset of death (Su and Scheffrahn 1998).

Although the slow-acting characteristic for CSIs against termites is desirable for the complete distribution of the AI into the vast colony for its elimination, the lengthy time required for the hexaflumuron baits to kill a colony could become its shortcoming on some occasions. The time period for such termite baits to eliminate a colony may be divided into three segments: 1) time required for the discovery of bait stations by termites, 2) time required for termites to ingest lethal dose, and 3) time required for termites to begin molting (thereby allowing the ingested CSIs to interfere with successful molting, leading to the death of the individual). The relatively more recent use of noviflumuron has shortened the $2^{nd}$ segment (the time required to ingest a lethal dose). Noviflumuron is more lethal than hexaflumuron, and a smaller amount (and thus the time needed for ingesting lethal does) is required to reach the lethal dose. Because the effects of CSIs do not take place until molting process begins, the $3^{rd}$ time segment remains the same when CSIs are used.

In this invention, the hyperecdysonism of ecdysone and 20E against *R. flavipes* and *C. formosanus* is described for the first time. These two termite species represent the most economically important genera of termites in the world. According to the subject invention, ecdysteroids and ecdysteroid agonists can be used in bait matrices to cause delayed lethality of termite workers, leading to the elimination of a colony. Use of ecdysteroids or these ecdysteroid agonists has an advantage over CSIs because ecdysteroids actively induce molting instead of passively waiting for termites to molt before the effects can take place. Thus, the subject invention advantageously (and surprisingly) removes (or reduces) the $3^{rd}$ segment of time required for termite colony elimination. Ecdysteroids or the subject ecdysteroid agonists can be also used synergistically in combination with CSIs in baits so that termites that are exposed to a sublethal dose are induced to molt, yet the molting process is inhibited by the CSI.

Certain ecdysone analogs, which are growth regulators, may be more effective against certain species of termites. Many insect growth regulators (IGRs) can also be species-specific. Thus, they can be selected and optimized for a given situation. Prior to the disclosure of the subject invention, ecdysteroids and analogs thereof, other than halofenozide, were not investigated for their ability to control termites. However, in light of the disclosure of the subject invention, one will now consider ecdysteroids, such as ecdysone, analogs thereof, and byproducts thereof for use in termite control programs. In contrast to the state of the art prior to the subject invention, the fact that the natural hormones ecdysone and 20E showed positive results will now lead those skilled in the art to believe and expect that other ecdysone agonists, especially those having desirable structural characteristics, can now be used to advantageously control termites. In preferred embodiments, one can use ecdysone and 20E in baits to induce hyperecdysonism in foraging worker caste (and nonforaging by trophallaxis) subterranean termites.

With the foregoing considered, examples of termite species that can be targeted (selectively) by use of the subject methods include *Coptotermes formosanus, Reticulitermes flavipes, R. hesperus, R. virginicus, R. tibialis*, and *Heterotermes aureus*, as well as termite species of the families (and pest genera) Mastotermitidae (*Mastotermes* species), Hodotermitidae (*Anacanthotermes, Zooterinopsis* species), Rhinotermitidae (*Coptotermes, Heterotermes, Reticulitermes, Psammotermes, Prorhinotermes, Schedorhinotermes* species), Kalotemiitidae (*Glyptotermes, Neotermes, Cryptotermes, Incisitermes, Kalotermes, Marginitermes* species), Serritermitidae, and Termitidae (*Pericapritermes, Allodontermes, Microtermes, Odontotermes, Nasutitermes, Termes, Ainitermes, Globitermes, Microcerotermes* species), Termopsidae (*Hodotermopsis, Zooterinopsis* species), and other pest species of termites. Preferably, methods of the subject invention are used to target subterranean termites.

The subject invention can be practiced in many ways. Some preferred apparatuses are described in WO 93/23998, U.S. Pat. No. 6,370,812, and U.S. Pat. No. 6,397,516. Some embodiments of the subject invention can include a housing that is designed to enclose a monitoring device and/or toxicant-containing matrix. This housing is useful for protecting the monitoring device and/or toxicant-containing matrix from the environment. The monitoring device or matrix can be enclosed within the housing in such a manner so they can be removed with minimal disruption to the foraging termites. This housing is preferably made from a durable, non-biodegradable material. Preferably, once infested by termites, the monitoring device can be gently removed from the soil or from the station housing (it is advantageous to utilize a station housing to minimize disruption to foraging tunnels). Upon removal of the monitoring device, a toxicant-containing matrix, comprising an ecdysteroid or an analog thereof (and CSI if desired), can then be placed in the station housing. The monitoring device and the toxicant matrix preferably comprise cellulose.

Various materials can be used, if desired, to encase the toxicant-containing matrix. This method for packaging the toxicant-containing matrix can also be used to create "dose-packs" that precisely provide the appropriate amount of toxicant. "An effective amount" of the subject ecdysteroid toxicant can be administered that is sufficient to kill, make sick, and/or prevent termite feeding of the structure or area being protected. "An effective amount" also distinguishes over naturally occurring (relatively very low) levels of the ecdysone or analog thereof that might be found in nature. An "effective amount" for termite control can also distinguish over natural or non-orally administered amounts of ecdysone that cause the normal termite molting process.

Depending on the MAC and CSI used (or if a CSI is used) and on the totality of circumstances for a given application, the ecdysteroid of the subject invention can be administered/made available to foraging worker termites (is present in the toxicant matrix) at a concentration of less than 10,000 ppm, at or below 7,500 ppm, at or below 5,000 ppm, and at or below 1,000 ppm. Also preferred are concentrations of less that 4,000 ppm. With these sample "ceilings" in mind, sample "floors" can be determined and include any of the concentrations specifically exemplified herein. For example, a preferred concentration range for embodiments using halofenozide (and depending on the CSI used) is 2500-5000 ppm.

Again, there are a variety of methods and apparatuses that can be utilized to practice the subject invention. The precise methods and apparatuses can be selected for optimal control of a particular target pest and environmental setting. Such applications would be apparent to a person skilled in this art using the teachings provided herein. For example, for particularly "shy" species of termites, a toxicant of the subject invention can be selected accordingly and used in the hermetically sealed baits described in WO 03/082000, US-2003-0177689-A1, and U.S. Pat. No. 6,857,223. Bait stations using the subject toxicants can also be made more "attractive" to termites (generally and/or specifically) by using the pheromones and semiochemicals and non-cellulose polymer delivery devices of WO 03/092376 and US-2003-0180343-A1. Electronic monitoring can also be employed in some embodiments of the subject invention. See e.g. U.S. Pat. Nos. 6,404,210; 6,052,066; and 5,815,090.

The subject invention includes combinations and mixtures of one or more types of MACs/ecdysteroids (and analogs) together with combinations and mixtures of one or more types of CSIs (both hexaflumuron and noviflumuron, for example). Furthermore, the two (or more) active ingredients ("AIs") of the subject invention need not be co-administered or provided at exactly the same time. The subject invention includes sequential administration of at least one of the AIs followed by, in an effective time period to allow for the enhanced action of the subject invention, administration of at least one of the other class of AIs. For example, the MAC could be provided first. At the desired time (for example, when sufficient time has elapsed to allow molting to be initiated), the CSI could then be provided. The CSI could also be provided first (to allow for dispersement in the colony, for example). The MAC/ecdysteroid/ecdysteroid analog could then be provided (for example, to initiate molting and to provide for enhanced kill/control of the termites). Factors such as timing and dosage can be optimized, according to the subject invention (for example, to effect control of the entire colony or colonies, to ensure adequate dispersal through the colony, and the like.

All patents, patent applications, provisional applications, and publications referred to or cited herein are incorporated by reference in their entirety to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

EXAMPLE 1

Protocol for Deeding Ecdysone to Subterranean Termites and Determining the Effects Thereof Termites were collected from three colonies each of C. formosanus and R. flavipes and were held in the laboratory at 26±1° C. and 98±2% RH before use. Technical grade ecdysone was dissolved in methanol to obtain 0.1, 1, 10, 100 and 1,000-ppm solutions by serial dilution. Methanol solutions (i.e., 0 ppm AI) were used as untreated controls. Each concentration solution (0.2 ml) was pipetted onto 55-mm-diameter Whatman No. 1 filter paper fitted into 5-cm-diameter glass Petri dishes and allowed to evaporate overnight.

This filter paper served as the cellulose food source for twenty-five termites, plus one soldier for R. flavipes or three soldiers for C. formosanus, which were introduced into each Petri dish after moistening the filter paper with 0.175 ml deionized water. For each species, two subsamples each of three colonies were used per concentration for a total of 72 experimental units. The bioassay units was held at 26±1° C. Observation was made daily for 12 days. Termites showing symptoms of incomplete molting were counted, and dead termites were removed from each unit. Because affected termites did not recover, they were included in mortality data. For each treatment and species combination, mean percent termites showing symptoms of incomplete molting and mortality among concentrations at 12 day were arcsine-root transformed and subjected to the analysis of variance (ANOVA). Significant differences ($\alpha=0.05$) among concentrations were separated using Fisher's least significant difference (LSD) test (SAS Institute 1999).

EXAMPLE 2

Results of Feeding Ecdysone to Subterranean Termites

Symptoms of hyperecdysonism (incomplete molting) were evident for both termite species after exposure to ecdysone at 1,000 ppm (Table I). After approximately 7 days of exposure, some termites exhibited the "jackknife" position due to the incomplete molting. The symptoms were similar to those exposed to the chitin synthesis inhibitor, hexaflumuron, as reported by Su & Scheffrahn (1993), or those observed from larval Coleopterans and Lepidoptera when treated with ecdysone agonists, where death occurs after premature molts are initiated but not terminated (Dhadialla et al. 1998). This is the only second time such incomplete molting symptom was recorded from termites (the first time being those caused by CSIs). With CSIs, termite molting was inhibited after ecdysone initiated the natural molting under a pre-set biological schedule. With the ecdysone exposure as described in this experiment, termites were artificially induced to premature molting without a successful termination. This is the reason why the symptoms of incomplete molting appeared faster in ecdysone (7 days) than in CSIs (4-8 weeks). Significant mortalities at 12 day were recorded for both termite species exposed to ecdysone at >100 ppm (Table I), with a large proportion of R. flavipes showing symptoms of hyperecdysonism. Surprisingly, 100% mortality was recorded from C. formosanus exposed to 100-ppm ecdyson. C. formosanus is generally less responsive to IGRs than R. flavipes, but with ecdyson, this appears to be the reverse.

TABLE I

Percent termites exhibiting incomplete molting (±SE) and mortality (±SE)
of R. flavipes and C. formosanus after 12-day exposure to ecdysone.

| Concentration | % Incomplete Molting | | % Mortality | |
|---|---|---|---|---|
| (ppm) | R. flavipes | C. formosanus | R. flavipes | C. formosanus |
| 0 | 0.00 ± 0.00a | 0.00 ± 0.00a | 0.64 ± 0.64a | 0.60 ± 0.60a |
| 0.1 | 0.00 ± 0.00a | 0.00 ± 0.00a | 0.00 ± 0.00a | 1.79 ± 1.22a |
| 1 | 0.00 ± 0.00a | 0.00 ± 0.00a | 0.00 ± 0.00a | 1.19 ± 0.75a |
| 10 | 0.00 ± 0.00a | 2.38 ± 2.38a | 0.00 ± 0.00a | 11.31 ± 6.55a |
| 100 | 0.00 ± 0.00a | 8.33 ± 5.95a | 60.26 ± 18.06b | 100.00 ± 0.00b |
| 1,000 | 21.80 ± 14.10b | 3.57 ± 2.26a | 100.00 ± 0.00c | 93.45 ± 6.55b |

Means within a column followed by the same letter are not significantly different ($\alpha = 0.05$; ANOVA [SAS Institute 1999]).

EXAMPLE 3

Protocol for Feeding 20-Hydroxyecdysone to Subterranean Termites and Determining the Effects Thereof 20-hydroxyecdysone is an ecdysone byproduct. Technical grade 20-hydroxyecdysone (20E) was dissolved and used in the same manners as was ecdyonse, as discussed above in Example 1. The results are presented in the following example.

EXAMPLE 4

Results of Feeding 20-Hydroxyecdysone to Subterranean Termites

Symptoms of hyperecdysonism were evident for both termite species after exposure to 20E at 1,000 ppm (Table II). After approximately 7 days of exposure, some termites exhibited the "jackknife" position due to the incomplete molting, as discussed above in Example 2. As with ecdysone, 20E also caused incomplete molting at a faster rate than CSIs.

Significant mortality was recorded from R. flavipes exposed to >100 ppm 20E, with 100% mortality for those exposed to 1,000 ppm (Table II). C. formosanus was less responsive to 20E than R. flavipes, showing ca. 75% mortality at 1,000 ppm. Nonetheless, results of ecdysone and 20E were much superior than that for halofenozide, which caused only 50% mortality for C. formosanus at 10,000 ppm when tested under similar condition (Monteagudo and Su 2002).

EXAMPLE 5

Additive Effects of the MAC Insecticide Halofenozide when Combined with Chitin Synthesis Inhibitors (Hexaflumuron and Noviflumuron) and Tested in Feeding Choice Tests with Eastern Subterranean Termites (EST)

This Example summarize a series of laboratory trials that determined the survivorship, and feeding response of eastern subterranean termites (EST), Reticulitermes flavipes (Kollar) in oral ingestion choice tests with halofenozide. Tests were also conducted to evaluate the potential additive/synergistic effects of halofenozide (at various concentrations) when combined with the chitin synthesis inhibitors hexaflumuron or noviflumuron.

Test #1. Choice Feeding Bait Test, Halofenozide + Hexaflumuron. A paired choice feeding test was conducted to compare feeding response and resultant mortality caused by various combinations of technical grade halofenozide and hexaflumuron treated on filter paper (acetone carrier). The test apparatus consisted of two round plastic containers connected by a 7-cm long piece of 2.5-mm diameter (ID) tygon tubing. A known number of termite workers were introduced into a central harborage chamber (5.5 cm round container with ventilated lid) containing a vermiculite/sand/water mixture of ca. 1:1:1. The central harborage chamber was connected by the tygon tubing to the bait foraging chamber (without sand/vermiculite matrix) containing the paired feeding choices.

TABLE II

Percent termites exhibiting incomplete molting (±SE) and mortality (±SE)
of R. flavipes and C. formosanus after 12-day exposure to 20-hydroxyecdysone.

| Concentration | % Incomplete Molting | | % Mortality | |
|---|---|---|---|---|
| (ppm) | R. flavipes | C. formosanus | R. flavipes | C. formosanus |
| 0 | 0.00 ± 0.00a | 0.00 ± 0.00a | 1.28 ± 0.81a | 0.60 ± 0.60a |
| 0.1 | 0.00 ± 0.00a | 0.00 ± 0.00a | 0.64 ± 0.64a | 1.19 ± 0.75ab |
| 1 | 0.00 ± 0.00a | 0.00 ± 0.00a | 0.00 ± 0.00a | 10.12 ± 9.42bc |
| 10 | 0.00 ± 0.00a | 0.00 ± 0.00a | 0.64 ± 0.64a | 3.57 ± 2.26abc |
| 100 | 3.85 ± 1.40ab | 2.38 ± 1.19a | 76.19 ± 11.28b | 11.90 ± 5.43c |
| 1,000 | 7.69 ± 3.29b | 26.19 ± 6.09b | 100.00 ± 0.00c | 74.40 ± 3.62d |

Means within a column followed by the same letter are not significantly different ($\alpha = 0.05$; ANOVA [SAS Institute 1999]).

ESTs were given the choice to feed between untreated blocks of southern yellow pine (SYP) and treated filter paper. Halofenozide was tested individually at concentrations of 1250, 2500, and 5000 ppm. Hexaflumuron was tested at 5000 ppm, and also combined with each of the aforementioned concentrations of halofenozide. For comparative purposes, technical grade noviflumuron were also tested at 5000 ppm. After twelve days, all treatments were removed, oven-dried, and weighed for consumption. Filter paper was placed in all bioassay units that were held for fourteen more days. Surviving termites were then counted in each replicate. Thus, survival was counted at 26 days after initial exposure to the toxicant. Each treatment was replicated four times with 50 termites per replicate.

Figure 3:
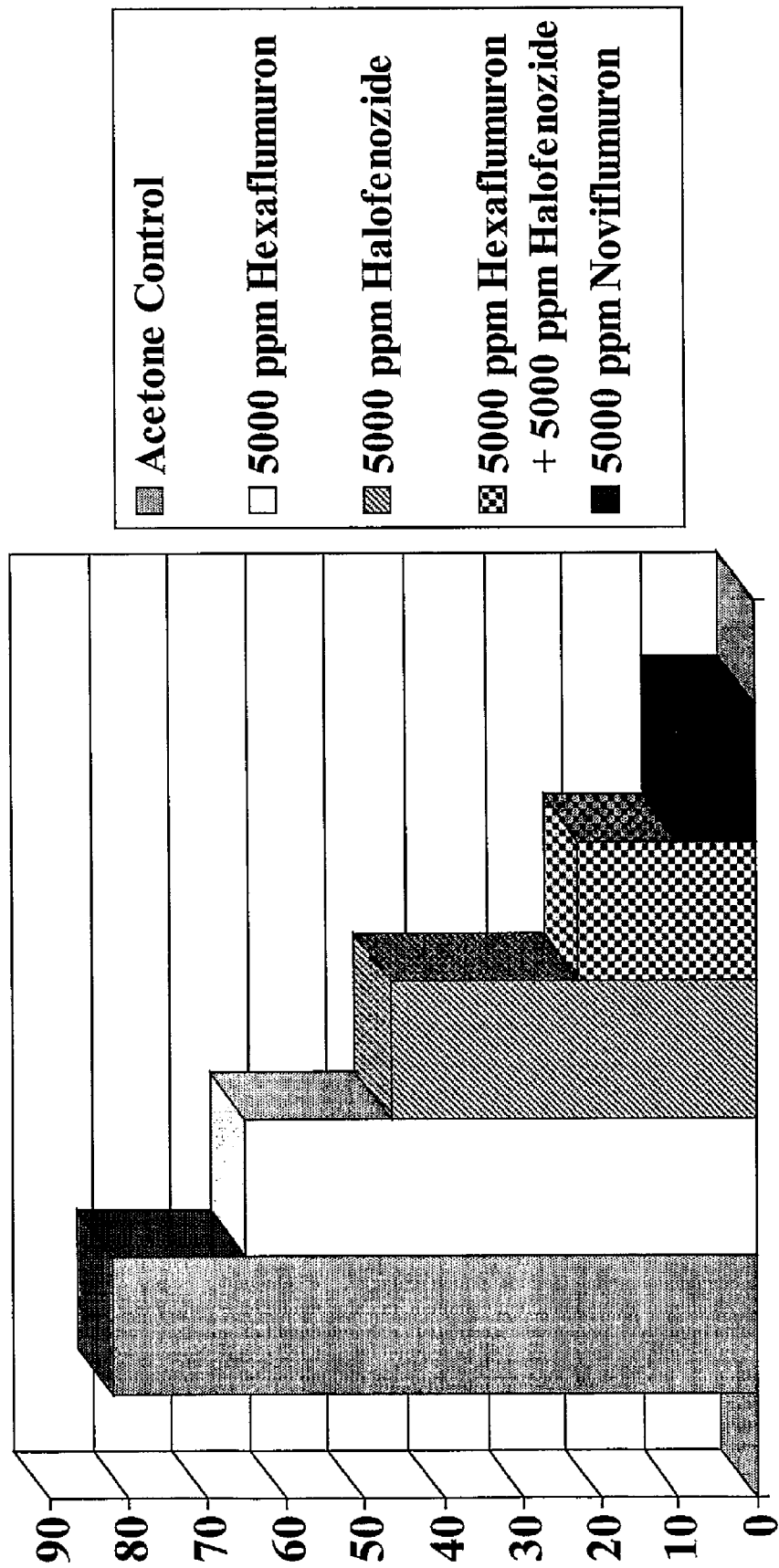
FIG. 3 illustrates the effects of halofenozide and hexaflumuron on eastern subterranean termites.

EST showed either significantly positive or neutral feeding response to all treatments on filter paper (FP) (Table III). As single treatments, 5000-ppm noviflumuron caused significantly greater efficacy than 5000-ppm halofenozide or 5000-ppm hexaflumuron after 26 days, while 5000-ppm halofenozide was significantly more efficacious than 5000 ppm hexaflumuron. The combination of 5000 ppm halofenozide +5000 ppm hexaflumuron caused a significantly lower level of survivorship when compared to either treatment alone. Moreover, the combination of halofenozide +hexaflumuron was significantly equal to the level of efficacy provided by 5000 ppm noviflumuron. Note that combining 5000 ppm hexaflumuron with lower concentrations of halofenozide did not cause significantly enhanced efficacy over 5000 ppm hexaflumuron alone. See FIG. 3, which graphically illustrates data from Table III.

TABLE III

Hexaflumuron + Halofenozide Test: Comparative Consumption and Resultant Survivorship of EST in Choice Tests Between Untreated SYP and Treated FP.

| Choice[a] | mg consumed after 12 days (Mean ± SEM)[b] | No. Survivors/50 after 26 days (Mean ± SEM)[c] | % Surviving |
|---|---|---|---|
| Acetone Control FP vs. SYP | 24.67 ± 4.52 a<br>8.98 ± 3.25 b | 41.00 ± 4.49 ab | 82.0 |
| Noviflumuron FP (5000) vs. SYP | 16.17 ± 3.64 a<br>1.77 ± 1.71 b | 5.00 ± 3.72 e | 10.0 |
| Hexaflumuron FP (5000) vs. SYP | 21.20 ± 2.06 a<br>9.28 ± 3.55 b | 32.5 ± 5.48 bc | 65.0 |
| Halofenozide FP (5000) vs. SYP | 9.33 ± 1.41 a<br>14.97 ± 3.85 a | 23.25 ± 7.88 d | 46.5 |
| Halofenozide FP (2500) vs. SYP | 18.70 ± 4.32 a<br>7.92 ± 2.13 a | 33.75 ± 6.56 bc | 67.5 |
| Halofenozide FP (1250) vs. SYP | 16.05 ± 3.39 a<br>9.49 ± 2.57 a | 45.00 ± 2.04 a | 90.0 |
| Hex (5000) + Halo FP (5000) vs. SYP | 13.92 ± 1.53 a<br>6.45 ± 2.20 b | 11.25 ± 3.75 e | 22.5 |
| Hex (5000) + Halo FP (2500) vs. SYP | 13.06 ± 2.58 a<br>13.27 ± 2.43 b | 26.25 ± 2.56 cd | 52.5 |
| Hex (5000) + Halo FP (1250) vs. SYP | 21.53 ± 5.32 a<br>5.97 ± 3.44 a | 27.25 ± 6.65 cd | 54.5 |

[a]Each choice test replicated four times (50 termites/rep)
[b]Within each choice test, pairs followed by the same letter are not significantly different (LSD; p > 0.10)
[c]Means followed by the same letter are not significantly different (LSD; p > 0.10)

Test #2. Choice Feeding Bait Test, Halofenozide +Noviflumuron. A standard paired choice feeding test using the same methods described in Test #1 was conducted to compare feeding response and resultant mortality caused by various combinations of technical grade halofenozide and noviflumuron treated on filter paper (acetone carrier). EST were given the choice to feed between untreated blocks of southern yellow pine (SYP) and treated filter paper. Halofenozide and noviflumuron were tested individually at concentrations of 5000 ppm. Five thousand ppm (5000-ppm) noviflumuron was also tested in combination with 1250, 2500, or 5000 ppm halofenozide. After fourteen days, all treatments were removed, oven-dried, and weighed for consumption. Because of the rapid activity of noviflumuron, surviving termites were also counted in each replicate after only 14 days of feeding. Each treatment was replicated four times with 50 termites per replicate.

Figure 4:
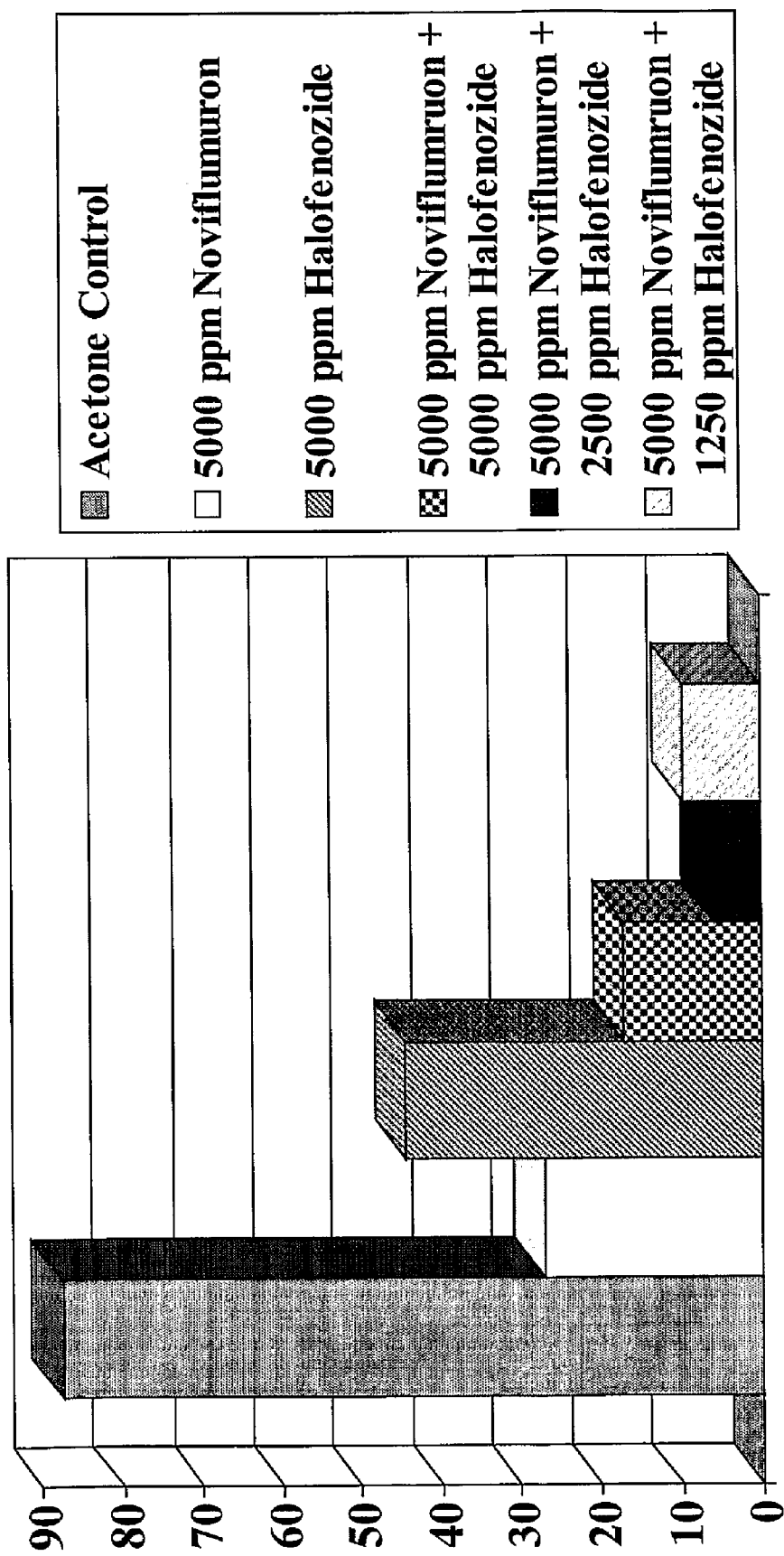
FIG. 4 illustrates the effects of halofenozide and noviflumuron on eastern subterranean termites.

Similar to results in Test #1, there was no significant repellency noted for any treatment, although there was numerically less acceptance of FP with 5000-ppm halofenozide (Table IV). After only fourteen days, 5000 ppm noviflumuron had already provided highly significant efficacy (only 27% survivorship). The single treatment of 5000-ppm halofenozide was also causing significant impact on survivorship after 27 days. However, the addition of halofenozide to noviflumuron appeared to boost speed of activity even further, especially when the two lowest concentrations of halofenozide were added. This can also be seen graphically in FIG. 4. The most effective combination was 5000 ppm noviflumuron +2500 ppm halofenozide, which caused significantly greater efficacy than either 5000 ppm of noviflumuron or halofenozide tested alone.

TABLE IV

Noviflumuron + Halofenozide Test: Comparative Consumption and Resultant Survivorship of EST in Choice Tests Between Untreated SYP and Treated FP.

| Choice[a] | mg consumed after 14 days (Mean ± SEM)[b] | No. Survivors/50 after 14 days (Mean ± SEM)[c] | % Surviving |
|---|---|---|---|
| Acetone Control FP vs. SYP | 25.88 ± 3.70 a<br>5.15 ± 1.00 b | 43.75 ± 3.61 a | 87.5 |
| Noviflumuron FP (5000) vs. SYP | 14.58 ± 2.20 a<br>2.58 ± 1.03 b | 13.50 ± 3.52 bc | 27.0 |
| Halofenozide FP (5000) vs. SYP | 10.12 ± 1.48 a<br>8.35 ± 3.91 a | 22.25 ± 5.36 b | 44.5 |
| Novi (5000) + Halo FP (5000) vs. SYP | 7.53 ± 1.14 a<br>8.56 ± 4.52 a | 8.50 ± 5.44 cd | 17.0 |
| Novi (5000) + Halo FP (2500) vs. SYP | 8.28 ± 2.45 a<br>4.94 ± 2.24 a | 3.00 ± 3.00 d | 6.0 |
| Novi (5000) + Halo FP (1250) vs. SYP | 15.14 ± 2.20 a<br>1.63 ± 2.50 b | 4.75 ± 0.95 cd | 9.5 |

[a]Each choice test replicated four times (50 termites/rep)
[b]Within each choice test, pairs followed by the same letter are not significantly different (LSD; p > 0.10)
[c]Means followed by the same letter are not significantly different (LSD; p > 0.10)

Summary. Results of these studies indicate that the combination of halofenozide plus a CSI insecticide can cause enhanced activity when compared to either type of insecticide alone. The impact of halofenozide appeared greater when combined with hexaflumuron, although a boost in speed of activity was also seen in combination with noviflumuron. For 5000-ppm hexaflumuron, a concentration of 5000-ppm halofenozide was needed to cause significant additive effects within 26 days. Lower concentrations of halofenozide (2500-1250 ppm) enhanced 5000-ppm noviflumuron within 14 days. While halofenozide might have a tendency to cause less acceptance of termite bait when compared to hexaflumuron or noviflumuron alone, significant repellency was not observed for any concentration of halofenozide in this study.

EXAMPLE 6

Additive Effect of the MAC Insecticide Halofenozide when Combined with Noviflumuron and Tested in Forced Feeding Tests with *Amitermes wheeleri*

This Example summarize a laboratory trial that determined the survivorship, and feeding response of *Amitermes wheeleri* in oral ingestion choice tests with halofenozide, noviflumuron and combination of the two active ingredients. *Amitermes wheeleri* is in the termite family (Termitidae), which is a different classification than the eastern subterranean termite (family Rhinotermitidae) shown in Example 5.

A forced feeding test was conducted to compare mortality caused by different active ingredients treated on purified cellulosic bait. The test apparatus was the same as that described in Example 5. Noviflumuron was tested on the bait at 5000-ppm concentration, and also in combination with 5000-ppm Halofenozide. Blank bait was also tested. Surviving termites were also counted at 28 days after initial exposure to the toxicant. Noviflumuron reduced termite survivorship in half when compared to the blank control. However, the combination of noviflumuron and halofenozide caused 100% kill, which again suggests that halofenozide can enhance the speed of efficacy for CSI insecticides.

TABLE V

Hexaflumuron + Halofenozide Test: Comparative Consumption and Resultant Survivorship of *Amitermes wheeleri* in Forced Feeding Bait Tests.

| Treatment | No. Survivors/30 after 28 days | % Surviving |
|---|---|---|
| Blank Cellulosic Bait | 26 | 87 |
| Cellulosic Bait with 5000 ppm noviflumuron | 12 | 43 |
| Cellulosic Bait with 5000 ppm noviflumuron + 5000 ppm halofenozide | 0 | 0 |

REFERENCES

Chapman, R. F. 1976. The insects. Structure and function. Elsevier, N.Y.

Darvas, B., L. Polgár, M. H. Tag El-Din, K. Eröss & K. D. Wing. 1992. Developmental disturbances in different insect orders caused by an ecdysteroid agonist, RH 5849. J. Econ. Entomol. 85: 2107-2112.

Dhadialla, T. S., G. R. Carlson & D. P. Le. 1998. New insecticides with ecdysteroidal and juvenile hormone activity. Annu. Rev. Entomol. 43: 545-569.

Haverty, M. I. 1977. The proportion of soldiers in termite colonies: a list and a bibliography (Isoptera). Sociobiology 2: 199-216

Hrdý, I. 1973. Effect of juvenoids on termites and honeybees. Proc. 7th Int'l. Congr. IUSSI, London 1973, pp. 158-161.

Hrdý, I. & J. Křeček. 1972. Development of superfluous soldiers induced by juvenile hormone analogues in the termite, *Reticulitermes lucifugus santonensis*. Insectes Soc. 19: 105-109.

Lüscher, M. 1960. Hormonal control of caste differentiation in termites. Ann. New York Acad. Sci. 89: 549-563.

Lüscher, M. & P. Karlson. 1958. Experimentelle auslösung von häutungen bei der termite *Kalotermes flavicollis* (Fabr.). J. Insect Physiol. 1: 341-345.

Monteagudo, E., and N.-Y. Su. 2002. Evaluation of halofenozide as a bait toxicant against eastern subterranean termite (Isoptera: Rhinotermitidae). Annual Mtng. Entomol. Soc. America, Ft. Lauderdale, Fla. Nov. 17-20.

Nation, J. L. 2002. Insect Physiology and Biochemistry. CRC Press, Boca Raton, Fla.

Raina, A. K., Y. I. Park & Z. Hruska. 2003. Ecdysone agonist halofenozide affects corpora allata and reproductive physiology of the Formosan subterranean termite, *Coptotermes formosanus*. J. Insect Physiol. 49: 677-683.

SAS Institute. 1999. SAS/STAT guide for personal computers, $8^{th}$ ed. SAS Institute, Cary, N.C.

Su, N.-Y. 1994. Field evaluation of a hexaflumuron bait for population suppression of subterranean termites (Isoptera: Rhinotermitidae). J. Econ. Entomol. 87: 389-397.

Su, N.-Y. 2003. Baits as a tool for population control of the Formosan subterranean termite. Sociobiology 41: 177-192.

Su, N.-Y., & R. H. Scheffrahn. 1990. Potential of insect growth regulators as termiticides: A review. Sociobiology 17: 313-328.

Su, N.-Y., & R. H. Scheffrahn. 1993. Laboratory evaluation of two chitin synthesis inhibitors, hexaflumuron and diflubenzuron, as bait toxicants against Formosan and eastern subterranean termites (Isoptera: Rhinotermitidae). J. Econ. Entomol. 86: 1453-1457.

Su, N.-Y., & R. H. Scheffrahn. 1998. A review of subterranean termite control practices and prospects for integrated pest management programs. Integrated Pest Management Reviews 3: 1-13.

Wilson, E. O. 1971. The Insect Societies. Belknap Press, Cambridge, Mass.

Wing, K. D., R. A. Slawecki & G. R. Carlson. 1988. RH 5849, a nonsteroidal ecdysone agonist: Effects on larval *Lepidoptera*. Science 241: 470-472.

The invention claimed is:

1. A composition for controlling termites wherein said composition comprises a molt-accelerating compound and a chitin synthesis inhibitor, wherein the molt-accelerating compound is an ecdysteroid analog methoxyfenozide, and wherein the chitin synthesis inhibitor is noviflumuron.

2. The composition of claim 1 wherein said composition is in a form selected from a cellulosic bait, a dust, and a liquid formulation.

3. The composition of claim 1 wherein said composition is in a bait in a durable housing.

4. The composition of claim 1 wherein said composition is in a hermetically sealed bait.

* * * * *

UNITED STATES PATENT AND TRADEMARK OFFICE
CERTIFICATE OF CORRECTION

| | |
|---|---|
| PATENT NO. | : 7,998,496 B2 |
| APPLICATION NO. | : 10/589770 |
| DATED | : August 16, 2011 |
| INVENTOR(S) | : Nan-Yao Su, Paul Allen Neese and James Edward King |

It is certified that error appears in the above-identified patent and that said Letters Patent is hereby corrected as shown below:

Column 8,
Line 28, "Kalotemiitidae" should read --Kalotermitidae--
Lines 32-33, "Ainitermes" should read --Amitermes--
Line 34, "Zooterinopsis" should read --Zootermopsis--

Column 10,
Line 5, "Deeding" should read --feeding--

Signed and Sealed this
Fifteenth Day of November, 2011

David J. Kappos
*Director of the United States Patent and Trademark Office*